US00PP37142P2

(12) United States Plant Patent
Holtmaat

(10) Patent No.: US PP37,142 P2
(45) Date of Patent: Dec. 9, 2025

(54) ***RUDBECKIA* PLANT NAMED 'RUDBCHR650'**

(50) Latin Name: *Rudbeckia hirta*
Varietal Denomination: RUDBCHR650

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/037,008

(22) Filed: Jan. 24, 2025

(30) Foreign Application Priority Data

Jul. 29, 2024 (QZ) ..... PBR 20241776

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02; A01H 5/00; A01H 6/14
See application file for complete search history.

(56) References Cited

U.S. PATENT DOCUMENTS

PP30,727 P2 * 7/2019 Holtmaat ..... A01H 5/02
Plt./474

* cited by examiner

*Primary Examiner* — June Hwu
(74) *Attorney, Agent, or Firm* — Penny J. Aguirre

(57) ABSTRACT

A new cultivar of *Rudbeckia* plant named 'RUDBCHR650' that is characterized by its short plant height, its compact plant habit, its flowering that commences early in the season, its inflorescences with conspicuous brown discs and ray florets that are yellow and suffused with a lighter yellow color towards the apex.

2 Drawing Sheets

CROSS-REFERENCE TO RELATED APPLICATIONS

This application claims priority to European Community Plant Variety Office (CPVO) Plant Breeder's Rights Application No. 2024/1776 filed on Jul. 29, 2024, under 35 U.S.C. 119 (f), the entire contents of which is incorporated by reference herein. The Applicant received the information for the Plant breeders' rights application directly from the Inventor. This application is also co-pending with a U.S. Plant Patent Applications filed for plants derived from the same breeding program that are entitled Rudbeckia Plant Named 'RUDBDIV658' (U. S. Plant Pat. No. 36,815), Rudbeckia Plant Named 'RUDBSUN303' (U. S. Plant Pat. No. 36,816).

Botanical classification: *Rudbeckia hirta.*

Variety denomination: 'RUDBCHR650'.

BACKGROUND OF THE INVENTION

The present invention relates to a new and distinct cultivar of *Rudbeckia hirta* and will hereafter by referred to by its cultivar name, 'RUDBCHR650'. The new cultivar is an herbaceous perennial grown for use as a landscape plant.

'RUDBCHR650' was selected in July of 2021 by the Inventor from amongst seedlings in a trial field in Zuidwolde, Netherlands that had been planted with a mixture of seed derived from open pollination of numerous unpatented and unnamed proprietary plants of *Rudbeckia hirta* from the Inventor's breeding program. The exact parentage is therefore unknown.

Asexual propagation of the new cultivar was first accomplished under the direction of the Inventor by tissue culture using meristematic tissue in Heerhugowaard, The Netherlands in January of 2022. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBCHR650' as a unique cultivar of *Rudbeckia.*

1. 'RUDBCHR650' exhibits a short plant height.
2. 'RUDBCHR650' exhibits a compact plant habit.
3. 'RUDBCHR650' exhibits flowering that commences early in the season.
4. 'RUDBCHR650' exhibits inflorescences with conspicuous brown discs and ray florets that are yellow and suffused with a lighter yellow color towards the apex.

'RUDBCHR650' can be compared to the *Rudbeckia* cultivars 'RUDHT53' (U.S. Plant Pat. No. 30,727) and 'RUDHT37' (U.S. Plant Pat. No. 30,657). 'RUDHT53' and 'RUDHT37' are both similar to 'RUDBCHR650' in flower coloration. 'RUDHT53' and 'RUDHT53' differs from 'RUDBCHR650' in having a shorter plant height and flowers that are smaller in size and in commencing bloom later in the season. 'RUDHT37' differs from 'RUDBCHR650' in having a taller plant height and flowers that are larger in size and in commencing bloom later in the season.

'RUDBCHR650' can also be compared to the co-pending cultivars of *Rudbeckia*; 'RUDBDIV658' and 'RUDBSUN303'. Both are similar to 'RUDBCHR650' in having short plant heights and in commencing bloom early in the season. 'RUDBDIV658' differs from 'RUDBCHR650' in having inflorescences that are smaller in size with ray florets that are more yellow (less orange) in color towards the apex as they fade. 'RUDBSUN303' differs from 'RUDBCHR650' in having inflorescences with ray florets that are bi-colored.

BRIEF DESCRIPTION OF THE DRAWINGS

The accompanying color photographs illustrate the overall appearance and distinct characteristics of the new *Rudbeckia*. The photographs were taken of a 3-month-old plant of 'RUDBCHR650' as grown outdoors in a 17-cm container in Zuidwolde, The Netherlands.

The photograph in FIG. 1 provides a side view of 'RUDBCHR650' in bloom.

Figure 1:
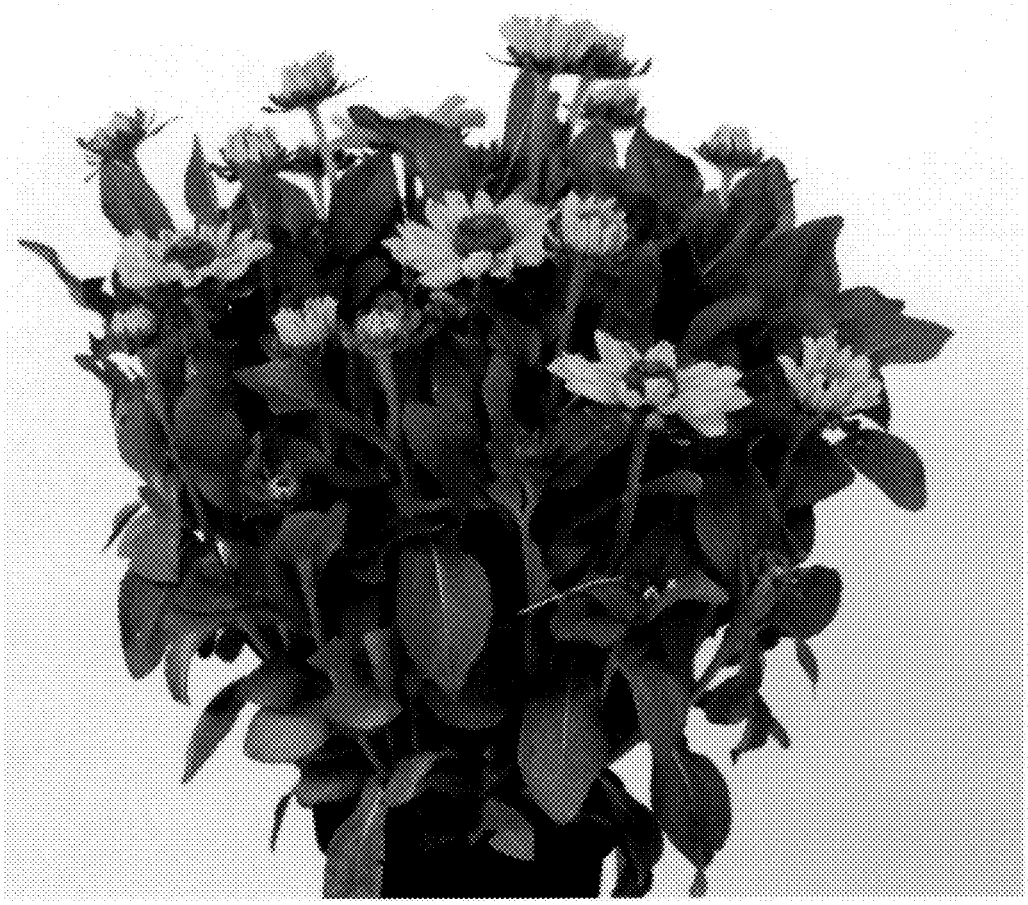
Figure 2:
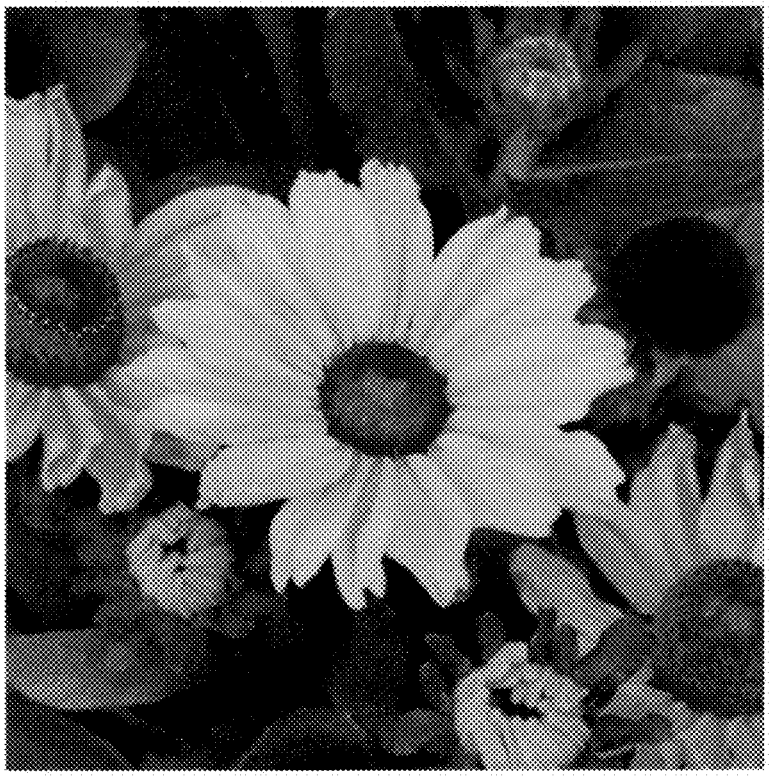

The photograph in FIG. 2 provides a close-up view of an inflorescence of 'RUDBCHR650'.

Figure 3:
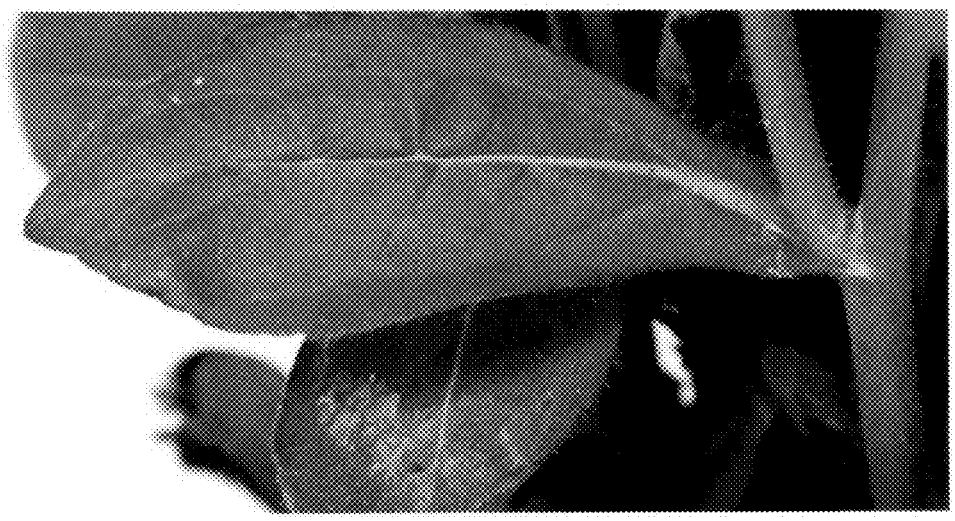

The photograph in FIG. 3 provides a close-up view of the foliage of 'RUDBCHR650'. The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 3-month-old plants of 'RUDBCHR650' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with the 2015 Colour Chart of the Royal Horticultural Society, London, England, except where general color terms of ordinary dictionary significance are used.

General Description:

*Blooming period*.—June to July in The Netherlands.

*Plant type*.—Perennial.

*Plant habit*.—Upright, compact.

*Plant shape*.—Obovate.

*Height and spread*.—Average of 44 cm in height from soil level to top of foliar plane and 48.8 cm in height from soil level to top of floral plane, 53.2 cm in diameter as a 3-month-old plant as grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Moderate vigorous.

Stem Description:

*Shape*.—Very slightly angled, 5-sided.

*Stem color*.—Young stems; 144B, mature stems; 144A, slightly flushed with 181A, angles 146B.

*Stem size*.—An average of 8.5 mm in diameter and an average of 23.7 cm in length.

*Stem surface*.—Moderately glossy and densely covered with strigose hairs an average of 2 mm in length and NN155D in color.

*Stem number*.—Average of 8 main stems, 5 lateral branches per main stem.

*Internode length*.—An average of 5.9 cm in length.

*Stem aspect*.—Main stems; average of 15° to vertical, lateral branches; average of 15° to main stems.

*Branching*.—Freely branching from base with lateral stems.

Foliage Description:

*Leaf shape*.—Obovate.

*Leaf division*.—Simple.

*Leaf base*.—Cuneate.

*Leaf apex*.—Broad bluntly acute.

*Leaf venation*.—Pinnate, color upper surface 147C, color lower surface 146B.

*Leaf margins*.—Coarsely shallowly crenate-serrate, coarsely slightly undulate.

*Leaf attachment*.—Petiolate.

*Leaf arrangement*.—Alternate.

*Leaf size*.—Average of 14.4 cm in length and 6.9 cm in width.

*Leaf color*.—Young upper surface; 143B, young lower surface; 144A, mature upper surface; NN137B, mature lower surface; 147B.

*Leaf surface*.—Upper surface very slightly glossy, lower surface slightly glossy, both surfaces rough to the touch, densely pubescent with short strigose hairs; an average of 2 mm in length and 156D in color.

*Petioles*.—Average of 3.5 mm in length, flattened, average diameter at widest point 1 cm and at narrowest point 6 mm, upper and lower surface color; 145A, both surfaces slightly glossy and densely covered with strigose hairs; an average of 1.5 mm in length and 156D in color.

Flower Description:

*Type*.—Terminal capitulum, consisting of ray florets and disc florets.

*Capitulum number*.—9 per stem, up to 75 per plant.

*Lastingness of inflorescence*.—Average of 2 weeks, persistent.

*Capitulum size*.—Matures to about 3.3 cm in height and 9.9 cm in diameter, disc size is an average of 2.8 cm in diameter and 2 cm in height.

*Fragrance*.—None.

*Involucral bracts* (*phyllaries*).—Cuneate base, obtuse apex, narrow oblanceolate to narrow oblong in shape, entire margins, average of 32 arranged in 3 rows, rotate, slightly curved upward, 2.4 cm in length and 8 mm in width, color; upper surface when fully open 137A, margins NN137A, lower surface when fully open 138A to 138B, both surfaces slightly glossy and densely covered with strigose hairs; an average of 2 mm in length and NN155D in color, margins are moderately to densely covered with strigose hairs 1.5 mm in length and 156D in color.

*Receptacle*.—Broad ovate in shape, an average of 1.3 cm in height and diameter, 157B in color.

*Buds*.—Shape; broad ovate, immature ray florets pointed upward and slightly curled inwards, 2.8 cm in length, width; excluding involucral bracts 2.5 cm, including involucral bracts 4.8 cm, surfaces are matte and densely covered with strigose hairs, average length of hairs on immature ray florets 1 mm, average length of hairs on involucral bracts: 0.15 cm, colored white on involucral bracts; N155A, and colored greyed-yellow on immature ray florets; 160D, hairs on immature ray florets adpressed.

*Peduncle*.—Strong, straight on top of main flowering stem, average of 14.2 cm in length and 6.5 mm in diameter, color; 143A and 144B, surface moderately glossy and densely covered with short strigose hairs; an average of 2 mm in length and 156D in color.

*Ray Florets*.—Average of 18 (varying between 16 and 21), rotate around the disc, oblong to slightly obovate and moderately concave in shape, average of 4.6 cm in length and 2.3 cm in width, emarginate to praemorse apex, cuneate base, entire margins, both surfaces are glabrous and velvety, densely covered with very short adpressed hairs, 0.75 mm in length and 160D in color, held near horizontal, color; when opening upper surface 14A, half towards base 17A to 17B, when opening lower surface 13A, when fully open upper surface 17A, suffused with 14A towards apex, when opening lower surface 17B, central section 15B, veins 146C, upper surface fades (ages) to 17A, lower surface fades (ages) to 17B.

*Disc florets*.—Average of 1,500, 25 whorls arranged spirally on a conical receptacle, lower 87.5% fused into tube, tubular, upright, about 8 mm in length and 4 mm in width, tubular, upper 12.5% free, free lobes have entire margins, apices of free lobes acute and curled backwards, both surfaces glabrous and slightly glossy, color; when opening upper and lower surface N200A, lower half 147D, when fully open upper and lower surface N200A, free lobes 165B, lower half 147D, no spines, but a single bract is placed beside each disc floret; 1 per disc floret, flattened, an average of 7 mm in length and 1 mm in diameter, oblanceolate in shape, acute apex, narrowly cuneate base, color; apex 145A, top 176B, mid-section 145C to 145D, margins 176B, base 157A, margins 200B, matte surface and moderately pubescent with hairs; an average of 0.2 mm in length, 176B in color.

Reproductive Organs:

*Gynoecium*.—Pistil; 1, 6 mm in length, style; 4.5 mm in length, 155C in color, stigma; cleft, decurrent, 4 mm in diameter, 177A in color, ovary; N155C in color.

*Androecium*.—Stamens; 5, filaments; 3 mm in length, 155C in color, anther; narrow oblong in shape, 2.5 mm in length, 0.5 mm in width, 203A in color, pollen; moderate in quantity and 15A in color.

*Fruit/seed*.—None observed.

It is claimed:

1. A new and distinct cultivar of *Rudbeckia* plant named 'RUDBCHR650' substantially as herein illustrated and described.

* * * * *